United States Patent
Kamiyama

(10) Patent No.: US 9,855,025 B2
(45) Date of Patent: Jan. 2, 2018

(54) ULTRASONIC DIAGNOSTIC APPARATUS AND ULTRASONIC IMAGE PROCESSING APPARATUS

(75) Inventor: Naohisa Kamiyama, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 13/310,976

(22) Filed: Dec. 5, 2011

(65) Prior Publication Data

US 2012/0078105 A1 Mar. 29, 2012

Related U.S. Application Data

(63) Continuation of application No. PCT/JP2010/062723, filed on Jul. 28, 2010.

(30) Foreign Application Priority Data

Jul. 28, 2009 (JP) .................... 2009-175540

(51) Int. Cl.
*A61B 8/00* (2006.01)
*G01S 7/52* (2006.01)
(Continued)

(52) U.S. Cl.
CPC .............. *A61B 8/54* (2013.01); *A61B 8/5207* (2013.01); *G01S 7/5209* (2013.01);
(Continued)

(58) Field of Classification Search
CPC ...................................... A61B 8/14
(Continued)

(56) References Cited

U.S. PATENT DOCUMENTS 6,440,074 B1 * 8/2002 Averkiou ................. 600/443
2005/0101863 A1 * 5/2005 Kawagishi et al. .......... 600/443
(Continued)

FOREIGN PATENT DOCUMENTS

CN 1596832 A 3/2005
CN 101238754 A 8/2008
(Continued)

OTHER PUBLICATIONS

International Search Report corresponding to International Application No. PCT/JP2010/062723 dated Aug. 24, 2010.
(Continued)

*Primary Examiner* — Rochelle Turchen
(74) *Attorney, Agent, or Firm* — Ken I. Yoshida

(57) ABSTRACT

According to one embodiment, an ultrasonic diagnostic apparatus comprises a receiving unit which provides at least some of echo signals with reception delays that vary with ultrasonic transducers and adds each of the echo signals provided with the reception delays to acquire a reception beam includes a predetermined receiving direction and a reception focus and a control unit, the control unit controlling the transmission unit so that a transmission beam including a transmission direction and a transmission focus that are fixed is transmitted, the control unit also controlling the receiving unit by changing patterns of the reception delays and adding the respective patterns to at least some of the echo signals based on the transmission beam including the transmission direction and the transmission focus that are fixed in order to acquire reception beams different in receiving direction and reception focus.

9 Claims, 8 Drawing Sheets

(51) Int. Cl.
*G10K 11/34* (2006.01)
*A61B 8/13* (2006.01)
*A61B 8/08* (2006.01)
*G01S 15/89* (2006.01)

(52) U.S. Cl.
CPC ........ *G01S 7/52046* (2013.01); *G10K 11/346* (2013.01); *A61B 8/13* (2013.01); *A61B 8/483* (2013.01); *A61B 8/486* (2013.01); *A61B 8/488* (2013.01); *G01S 7/5206* (2013.01); *G01S 15/8979* (2013.01)

(58) Field of Classification Search
USPC .......................................... 600/437, 443, 447
See application file for complete search history.

(56) References Cited

U.S. PATENT DOCUMENTS

| | | | |
|---|---|---|---|
| 2007/0016049 A1 | 1/2007 | Kye | |
| 2008/0249405 A1* | 10/2008 | Kakee | ........................... 600/437 |
| 2009/0043208 A1* | 2/2009 | Hergum et al. | ................ 600/455 |
| 2009/0306510 A1* | 12/2009 | Hashiba et al. | .............. 600/447 |
| 2010/0280373 A1* | 11/2010 | Fan | ...................... A61B 8/0833 |
| | | | 600/439 |

FOREIGN PATENT DOCUMENTS

| | | |
|---|---|---|
| CN | 101238991 A | 8/2008 |
| JP | 2003-061964 A | 3/2003 |
| JP | 2004-313485 A | 11/2004 |
| JP | 2004-321274 A | 11/2004 |
| JP | 2006-320596 A | 11/2006 |
| JP | 2007-7045 A | 1/2007 |

OTHER PUBLICATIONS

Chinese Office Action with English Translation for Chinese Patent Application No. 201080014903.5 dated Apr. 28, 2013.

* cited by examiner

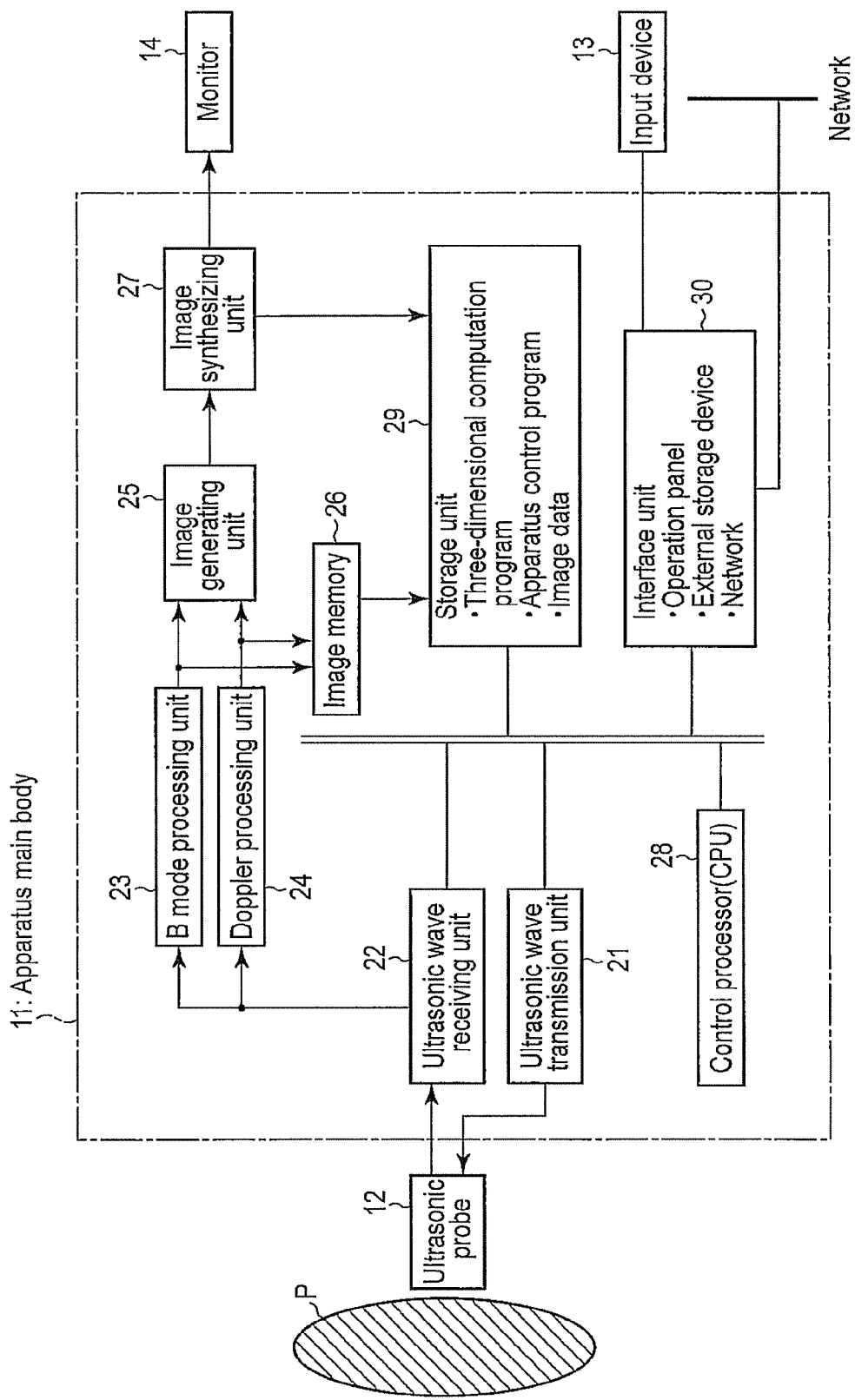
F I G. 1

Normal B mode image

Beam profile image

Normal B mode image

Beam profile image

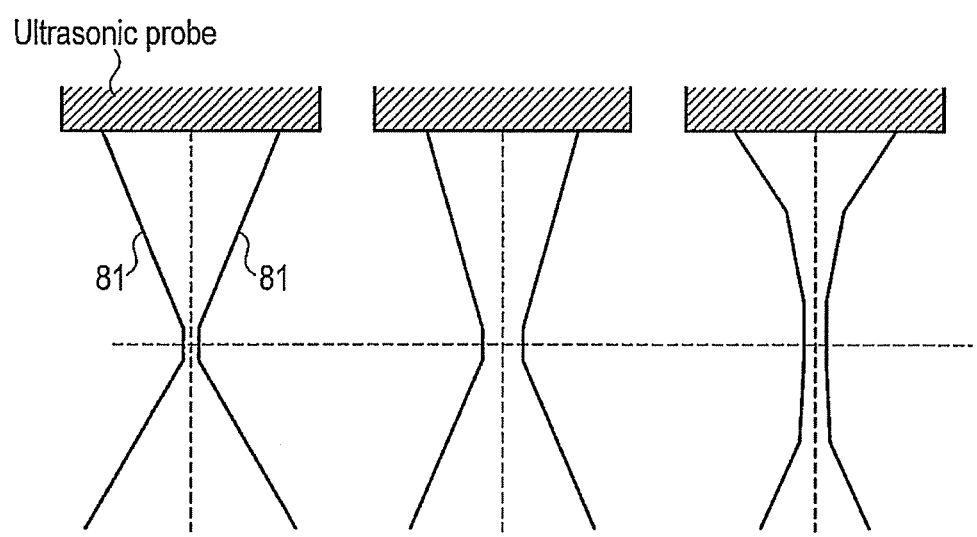
F I G. 12

ULTRASONIC DIAGNOSTIC APPARATUS AND ULTRASONIC IMAGE PROCESSING APPARATUS

CROSS REFERENCE TO RELATED APPLICATIONS

This application is a Continuation Application of PCT Application No. PCT/JP2010/062723, filed Jul. 28, 2010 and based upon and claiming the benefit of priority from prior Japanese Patent Application No. 2009-175540, filed Jul. 28, 2009, the entire contents of all of which are incorporated herein by reference.

FIELD

Embodiments described herein relate generally to an ultrasonic diagnostic apparatus and an ultrasonic image processing apparatus used to scan a subject with ultrasonic waves to form a tomogram of, for example, organs for an image diagnosis of a disease or the like.

BACKGROUND

An ultrasonic diagnostic apparatus is a diagnostic apparatus for displaying an image of information on the inside of a living body, and is inexpensive and requires no exposure to radiation as compared with other image diagnostic apparatuses such as an X-ray diagnostic apparatus and a computerized transverse axial tomography. Thus, the ultrasonic diagnostic apparatus is used as an apparatus useful for noninvasive real-time observations. The ultrasonic diagnostic apparatus is widely applied to the diagnoses of circulatory organs such as a heart, abdominal organs such as a liver and a kidney, peripheral blood vessels, gynecology, and breast cancer.

In general, the ultrasonic diagnostic apparatus transmits convergent ultrasonic waves (transmission beam) for one scan line one time, and receives signals focused in the transmission direction, thereby acquiring diagnostic information (ultrasonic image data) regarding parts on the scan line. Further, the ultrasonic diagnostic apparatus sequentially changes the scanning direction to repeatedly transmit and receive ultrasonic waves for the individual scan lines in a similar manner, thereby finally generating two-dimensional or three-dimensional diagnostic images. In recent years, a method (simultaneous reception) that obtains diagnostic information regarding parts on more than one scan line in one transmission has also been used. This method transmits convergent ultrasonic waves, and provides echo signals thus obtained with different reception delays to add delays in parallel more than once, thereby creating reception beams corresponding to more than one direction. In general, if a reception focus is set on the transmission direction, a highest quality diagnostic image can be obtained.

Meanwhile, the convergent ultrasonic waves used in transmission always have a focus. This focus is generally represented by a mark, on an image so that an operator can recognize the position and size of the focus. In general, spatial resolution is highest in the vicinity of the focus. Therefore, the operator changes and sets, for example, a focal position on an image in accordance with the position and size of a region of interest. The ultrasonic diagnostic apparatus changes a transmission delay pattern in accordance with, for example, the position of a set focus mark to change an actual transmission focus.

The position and shape of the transmission/reception focus influence the spatial resolution. Thus, for an examiner, details of the transmission/reception focuses are important information that influences the image quality. For example, regarding a first sound field (beam profile) from the left in FIG. 12 formed by a transmitted pulse, the degrees of in-focus or out-of-focus convergence can be visually recognized. Here, border lines 81 are contour lines of sound pressure in the sound field, and an echo signal inside the border lines 81 can be considered to be the main component of a diagnostic image. The first beam profile from the left in FIG. 12 and the second beam profile from the left in FIG. 12 have the same focal position. However, the aperture at the focus is narrower and the spatial resolution in this place is higher in the first beam profile from the left in FIG. 12 than in the second beam profile from the left in FIG. 12. The first sound field from the left in FIG. 12 and the third sound field from the left in FIG. 12 have the same spatial resolution at the focus. On the contrary, it is apparent that the beam profile including out-of-focus parts is narrower in the third sound field from the left in FIG. 12 and that the overall spatial resolution is higher in the third sound field from the left in FIG. 12.

However, the conventional ultrasonic diagnostic apparatus only provides information on the position where the focus is present, so that it is impossible to known, for example, the difference between the first sound field from the left in FIG. 12, the second sound field from the left in FIG. 12, and the third sound field from the left in FIG. 12. That is, according to the conventional ultrasonic diagnostic apparatus, it is impossible to intuitively known how the actual position and shape of the transmission/reception focus influence the image quality.

It has been made in view of such circumstances, and is directed to provide an ultrasonic diagnostic apparatus and an ultrasonic image processing apparatus that generate an image (beam profile image) regarding an actual sound field and enable direct visual recognition of, for example, the shape and focal position of a sound field formed in ultrasonic wave transmission/reception.

BRIEF DESCRIPTION OF THE DRAWINGS

FIG. 1 is a block configuration diagram of an ultrasonic diagnostic apparatus according to a first embodiment;

FIG. 12 is a diagram for illustrating sound fields in ultrasonic image collection.

DETAILED DESCRIPTION

Figure 2:
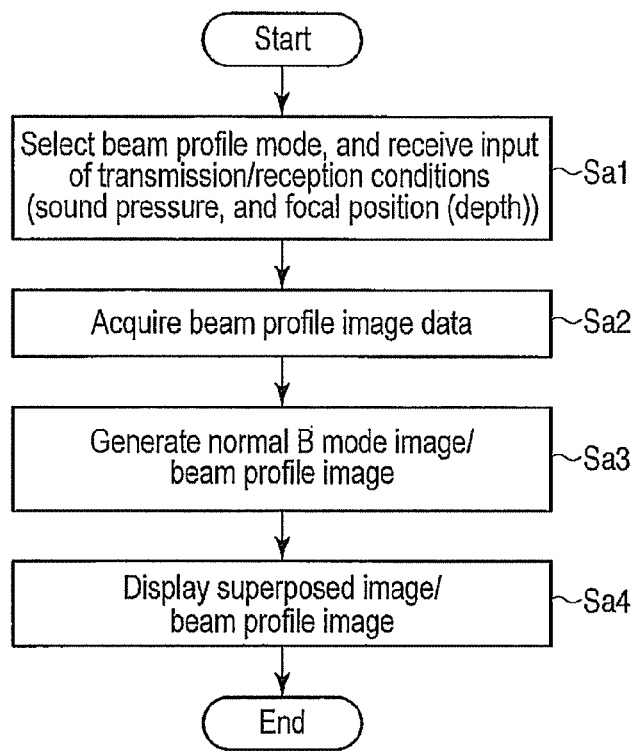
FIG. 2 is a flowchart showing the flow of beam profile image generating/displaying processing according to the first embodiment.

In general, according to one embodiment, an ultrasonic diagnostic apparatus comprises an ultrasonic probe which comprises ultrasonic transducers, each of the ultrasonic transducers generating ultrasonic waves in response to a supplied drive signal, and generating an echo signal in response to received ultrasonic waves, a transmission unit which supplies the drive signal to each of the ultrasonic transducers and thereby transmits, from the ultrasonic probe, a transmission beam based on a transmission direction and a transmission focus that are set, the drive signal being provided with a different transmission delay for each of the ultrasonic transducers, a receiving unit which provides at least some of the echo signals with reception delays that vary with the ultrasonic transducers and adds each of the echo signals provided with the reception delays to acquire a reception beam comprising a predetermined receiving direction and a reception focus, a control unit, the control unit controlling the transmission unit so that a transmission beam including a transmission direction and a transmission focus that are fixed is transmitted from the ultrasonic probe, the control unit also controlling the receiving unit by changing patterns of the reception delays and adding the respective patterns to at least some of the echo signals based on the transmission beam including the transmission direction and the transmission focus that are fixed in order to acquire reception beams different in receiving direction and reception focus, an image generating unit which uses the reception beams to generate a beam profile image regarding the transmission beam including the transmission direction and the transmission focus that are fixed and a display unit which displays the beam profile image, or a predetermined image generated by use of the beam profile image.

A first embodiment and a second embodiment will be described hereinafter with reference to the drawings. In the following explanation, components having about the same function and configuration are provided with the same reference signs, and are repeatedly explained only when necessary.

(First Embodiment)

FIG. 1 is a diagram showing a block configuration of an ultrasonic diagnostic apparatus according to the first embodiment. As shown, an ultrasonic diagnostic apparatus main body 11 comprises an ultrasonic probe 12, an input device 13, a monitor 14, an ultrasonic wave transmission unit 21, an ultrasonic wave receiving unit 22, a B mode processing unit 23, a Doppler processing unit 24, an image generating unit 25, an image memory 26, an image synthesizing unit 27, a control processor 28, a storage unit 29, and an interface unit 30.

The ultrasonic wave transmission unit 21, the receiving unit 22 and others provided in the apparatus main body 11 may be configured by hardware such as integrated circuits, but may be software programs in the form of software-like modules. The functions of the individual components are described below.

The ultrasonic probe 12 generates ultrasonic waves in accordance with a drive signal from the ultrasonic wave transmission unit 21. The ultrasonic probe 12 has piezoelectric transducers for converting reflected waves from a subject to an electric signal, matching layers provided in the piezoelectric transducers, a packing material or the like for preventing backward propagation of ultrasonic waves from the piezoelectric transducers. When convergent ultrasonic waves (transmission beam) are transmitted from the ultrasonic probe 12 to a subject P, the transmitted ultrasonic waves are sequentially reflected by discontinuities of acoustic impedance of body tissues, and received by the ultrasonic probe 12 as echo signals. The amplitude of the echo signal is dependent on the difference of acoustic impedance of the discontinuities which have reflected the ultrasonic waves. When a transmitted ultrasonic pulse is reflected by, for example, moving blood or the surface of the heart wall, the frequency of a resultant echo is shifted by a Doppler effect depending on a velocity component of a moving body in an ultrasonic wave transmission direction.

The input device 13 is connected to the apparatus main body 11. The input device 13 has various switches, buttons, and track balls as well as a mouse and a keyboard to load, into the apparatus main body 11, various instructions from the operator, conditions, an instruction to set a region of interest (ROI), and various image quality condition setting instructions.

In accordance a video signal from the image generating unit 25, the monitor 14 displays, as images, morphologic information on a living body and blood flow information.

The ultrasonic wave transmission unit 21 has a pulse generator, a transmission delay unit, and a pulser. The pulser repeatedly generates rated pulses for forming transmission ultrasonic waves at a predetermined rated frequency fr Hz (period; /fr second). The transmission delay unit provides each rated pulse of each transducer with a delay time (transmission delay) necessary to converge the ultrasonic waves into a beam form channel by channel and determine a transmission directivity (transmission direction). The pulse generator applies a drive signal (drive pulse) to the probe 12 in accordance with timing based on the rated pulse.

The ultrasonic wave receiving unit 22 has a preamplifier, an A/D converter, a reception delay unit, and an adder. The preamplifier amplifies, channel by channel, the echo signal loaded via the ultrasonic probe 12. The A/D converter converts the echo signal as an analog signal to a digital signal. The reception delay unit provides the echo signal of each transducer with a delay time (reception delay) necessary to determine a reception directivity (receiving direction). The adder then performs addition processing. As a result of this addition, a reflection component from the direction corresponding to the reception directivity of the echo signal is emphasized, and an overall beam for ultrasonic wave transmission/reception is formed by the reception directivity and the transmission directivity. Although not shown, a memory for storing the echo signal of each channel is provided before the reception delay unit.

On receipt of the echo signal from the receiving unit 22, the B mode processing unit 23 performs logarithmic amplification and envelope detection of the echo signal, and generates data which represents signal strength by the degree of brightness. The data is transmitted to the image generating unit 25, and displayed on the monitor 14 as a B mode image which represents the strength of reflected waves by brightness.

The Doppler processing unit 23 performs a frequency analysis of velocity information in accordance with the echo signal received from the ultrasonic wave receiving unit 22, extracts blood flow, tissue and contrast agent echo components attributed to the Doppler effect, and finds blood flow information including, for example, an average velocity, dispersion, and power for a large number of points. The obtained blood flow information is sent to the image generating unit 25, and displayed in color on the monitor 14 as an average velocity image, a dispersion image, a power image, and a combination of these images.

The image generating unit 25 converts a scan line signal sequence obtained by an ultrasonic scan to a scan line signal sequence in a general video format typified by television, thereby generating an ultrasonic diagnostic image as a display image. The image generating unit 25 is equipped with a storage memory for storing image data so that, for example, after a diagnosis, the operator can call the image recorded during an inspection. Data before entering the image generating unit 25 may be called "raw data".

The image memory 26 comprises a storage memory for storing the image data received from the image generating unit 25. The image data can be called by the operator, for example, after a diagnosis, and can be reproduced in the form of a still image or in the form of moving images. An output signal (referred to as a radio frequency (RF) signal) immediately after the ultrasonic wave receiving unit 22, an image luminance signal immediately after passed through the ultrasonic wave receiving unit 22, other raw data, and image data acquired via a network are stored in the image memory 26 as needed.

The control processor 28 functions as an information processor (computer), and is control means for controlling the operation of the ultrasonic diagnostic apparatus main body. The control processor 28 performs, for example, computation and control regarding various kinds of processing by reading, from the storage unit 29, a special program for enabling a beam profile image generating/displaying function and a special program for carrying out various kinds of calculation processing. In particular, the control processor 28 reads a transmission delay pattern and a reception delay pattern stored in the storage unit 29 to switch the transmission delay and the reception delay in accordance with the transmission direction and the receiving direction.

The following are stored in the storage unit 29: the special program for enabling the later-described beam profile image generating/displaying function; combined patterns for the transmission delay; combined patterns for the reception delay, a special program for executing various kinds of calculation processing such as later-described focal position calculation processing, processing for calculating a sound velocity within a subject (within a medium), feature amount calculation processing using the echo signal, and calculation processing for an index that indicates reliability; control programs for performing a predetermined scan sequence, image generation, and display processing; diagnostic information (e.g., patient IDs, doctor findings); a diagnostic protocol; transmission/reception conditions, and other data groups. If necessary, the storage unit 29 is also used to save images retained in the image memory 26. The data in the storage unit 29 can be transferred to external peripheral devices via the interface unit 30.

The interface unit 30 is an interface for the input device 13, the network, and a new external storage device (not shown). The interface unit 30 enables the data on the diagnostic image and analytic results obtained by this apparatus to be transferred to other apparatuses via the network.

(Beam Profile Image Generating/Displaying Function)

Now, the beam profile image generating/displaying function provided in the present ultrasonic diagnostic apparatus is described. This function generates a beam profile image as information that indicates a beam profile of the transmission beam actually transmitted to each scan line, and displays the beam profile image in a predetermined form.

FIG. 2 is a flowchart showing the flow of processing according to the beam profile image generating/displaying function (beam profile image generating/displaying processing). The contents of processing in each step are described below.

[Selection of Beam Profile Mode, and Setting of Transmission/Reception Conditions: Step Sa1]

First, a beam profile mode (mode for performing the beam profile image generating/displaying function) is selected via the input device 13, and transmission sound pressure and transmission/reception conditions of a focal position (depth) are input (step S1). In response to a selection/input instruction, the control processor 28 starts the special program and expands the program on the memory, thereby starting the beam profile mode and setting a voltage, a transmission delay, and a reception delay for enabling the various transmission/reception conditions.

[Acquisition of Beam Profile Image Data: Step S2]

Figure 3:
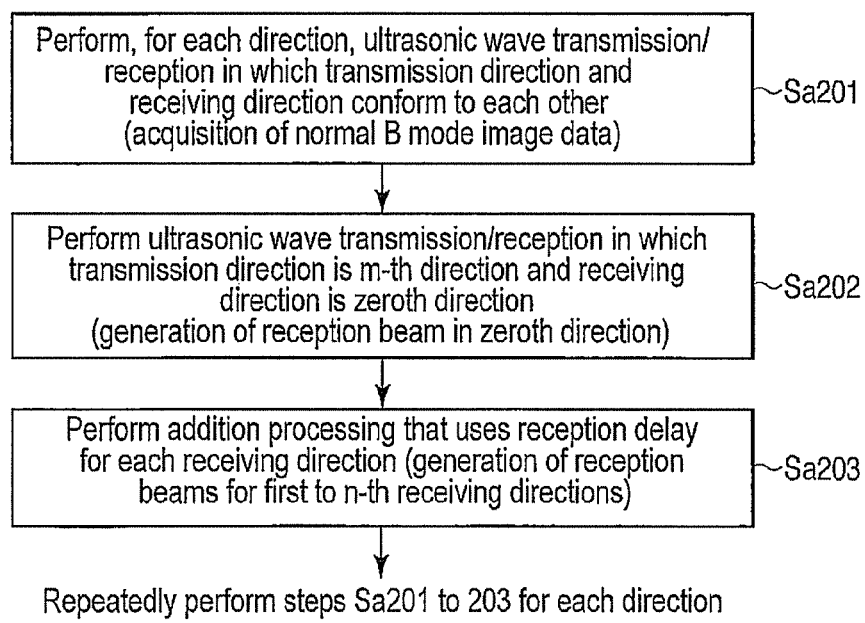
FIG. 3 is a flowchart showing the flow of beam profile image acquiring processing.
Figure 4:
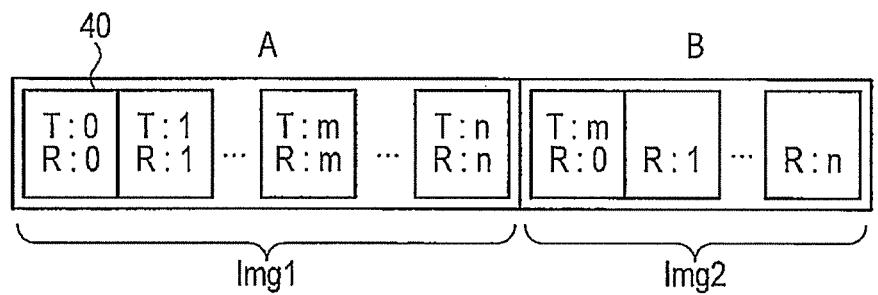
FIG. 4 is a diagram for illustrating the concept of the beam profile image acquiring processing according to the first embodiment.

FIG. 3 is a flowchart showing the flow of ultrasonic wave transmission/reception for acquiring beam profile image data. FIG. 4 is a diagram for illustrating the concept of ultrasonic wave transmission/reception for acquiring beam profile image data. In FIG. 4, one box 40 indicates one ultrasonic wave transmission/reception. In the ultrasonic wave transmission/reception corresponding to each box 40, T:i symbolically indicates setting of the transmission delay in an i direction in the ultrasonic wave transmission, and R:j symbolically indicates setting of the reception delay in a j direction in the ultrasonic wave transmission. i, j are integral numbers that respectively satisfy $0 \leq i \leq n$ and $0 \leq j \leq n$, and n is the last number of the scan line (thus, in the present embodiment, one two-dimensional image is formed by the (n+1) scan lines in n+1 directions from a direction 0 to a direction n).

First, the control processor 28 performs the ultrasonic wave transmission/reception in which the transmission direction and the receiving direction conform to each other (i.e., normal ultrasonic wave transmission/reception) for each of the n+1 scan lines corresponding to the scan line numbers zero to n (step Sa201). This transmission/reception is indicated as ultrasonic imaging (Img1) corresponding to a block A in FIG. 4. Normal B mode image data is acquired by the Img1.

Furthermore, ultrasonic wave transmission/reception in which the transmission direction is the m-th direction (note that m is a desired beam transmission direction for acquiring a beam profile image, and $0 \leq m \leq n$.) and the receiving direction is the zeroth direction is performed (step Sa202). That is, as shown in FIG. 4, ultrasonic wave transmission/reception in which a transmission delay in the m-th direction and a reception delay in the zeroth direction are set is performed. An echo signal acquired by the transmission/reception is recorded for each channel in the memory before the reception delay unit of the ultrasonic wave receiving unit 22, and the reception delay in the zeroth direction is added to the echo signal in the reception delay unit, so that an echo signal (reception beam) in which the zeroth direction is the receiving direction (scan line direction) is generated.

Using the recorded echo signal for each channel, the control processor 28 then performs addition processing that uses the reception delay for each receiving direction, and generates reception beams for the first to n-th receiving directions (scan line directions) (step Sa203). That is, as shown in FIG. 4, the control processor 28 adds the reception delay in the first direction to the echo signal for each channel which has been recorded in the memory before the reception delay unit and in which the transmission delay is set in the m-th direction, thereby generating a reception beam in which the first direction is the receiving direction (scan line direction). Similarly, using the recorded echo signal for each channel, the control processor 28 adds the reception delays in the second, third, . . . , n-th receiving directions, and generates reception beams for the respective receiving directions (scan line directions). The creation of the reception beams for the zeroth to n-th receiving directions is indicated as ultrasonic imaging (Img2) corresponding to a block B in FIG. 4. The Img2 acquires image (beam profile image) data correlated with a sound field beam profile for the transmission beam in which the m-th direction is the transmission direction.

It is preferable that a scan section in the Img1 for acquiring a normal B mode image be substantially the same as a scan section in the Img2 for acquiring a beam profile image.

In step Sa2, the acquisition of the beam profile image data for the transmission beam in which the transmission direction is the m-th direction has been described. For transmission beams of the other directions, beam profile image data can be acquired if similar processing is performed by setting Img3, Img4 . . . . In this case, if the operator inputs an instruction to change the transmission direction by use of, for example, the track ball attached to the input device 13, the transmission direction can be changed to any direction.

In the present embodiment, when the beam profile image data is generated (i.e., the Img2, or the subsequent Img3, Img4 . . . ), the echo signal for each channel obtained by the first ultrasonic wave transmission is recorded before reception and addition, and the reception delay for each receiving direction is used and added to this echo signal, and a reception beam for each direction is generated. The use of such a configuration allows an actually required time to be about one transmission time. Moreover, the additions using the reception delays in the respective receiving directions may be performed simultaneously (in parallel) by providing the reception delay units and the adders in parallel.

[Generation of B Mode Image/Beam Profile Image: Step Sa3]

The image data acquired in the imaging Img1 and the image data acquired in the imaging Img2 are subjected to logarithmic amplification and envelope detection processing in the B mode processing unit 23, and sent to the image generating unit 25. Using the received image data, the image generating unit 25 generates a normal B mode image corresponding to the Img1, and a beam profile image of the transmission beam for a direction m corresponding to the Img2 (step Sa3).

[Display of Superposed Image/Beam Profile Image: Step Sa4]

Figure 5:
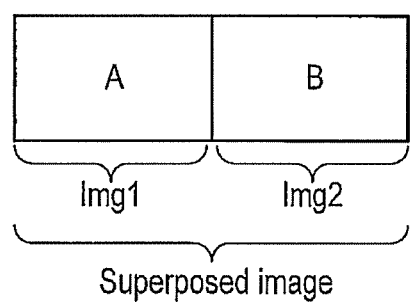
FIG. 5 is a diagram for illustrating the concept of the beam profile image acquiring processing according to the first embodiment.

As shown in FIG. 5, the image synthesizing unit 27 generates a superposed image by using the B mode image acquired by the Img1 and the beam profile image acquired by the Img2. For example, the image synthesizing unit 27 allocates a predetermined color to the beam profile image, and generates a superposed image in which the beam profile image is superposed on the B mode image by matching spatial positions (or a superposed image in which the B mode image is superposed on the beam profile image). Alternatively, the image synthesizing unit 27 reduces by half the gray-scale luminance values of both of the beam profile image and the B mode image, and generates a superposed image in which one of the images is superposed on the other.

The generated superposed image or beam profile image is, for example, independently displayed or displayed in parallel with the B mode image acquired by the Img1 (step Sa4).

Figure 6A:
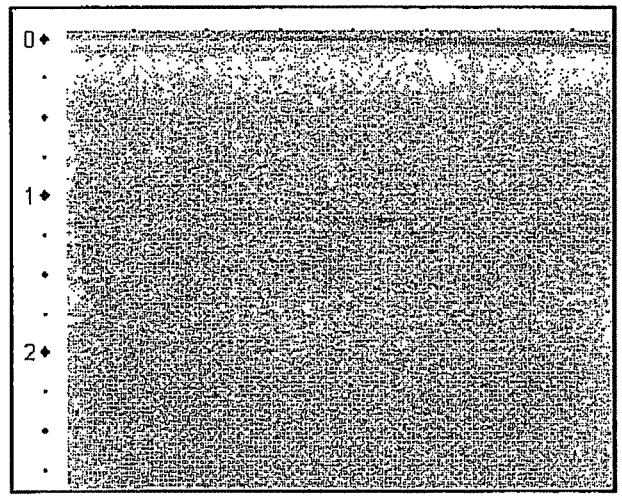
FIG. 6A is a view showing an example of a beam profile image.
Figure 6B:
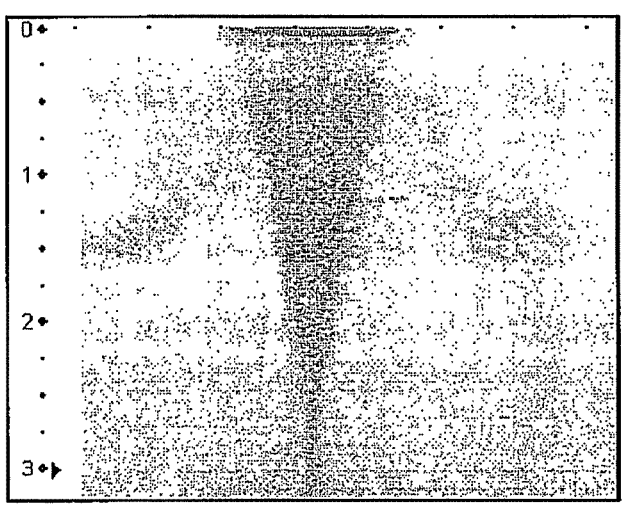
FIG. 6B is a view showing an example of a beam profile image.
Figure 7A:
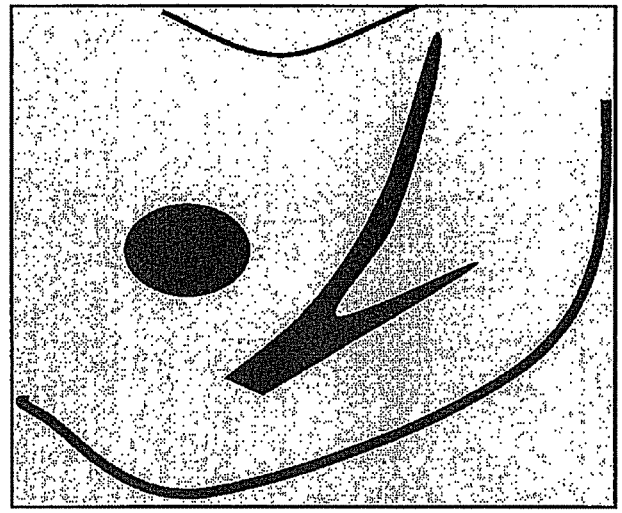
FIG. 7A is an illustration schematically showing a beam profile image.
Figure 7B:
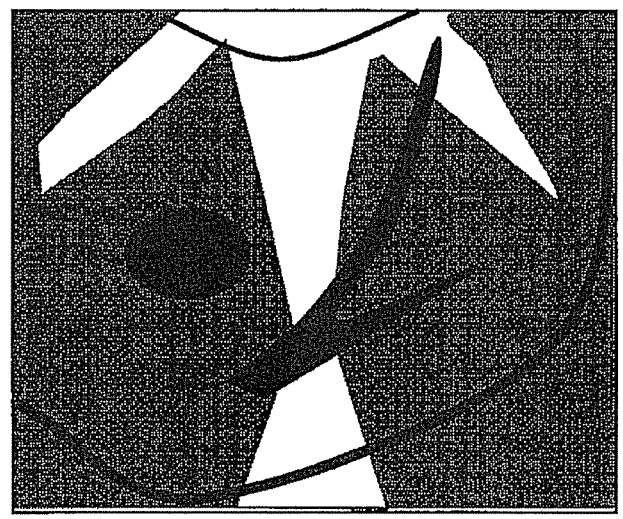
FIG. 7B is an illustration schematically showing a beam profile image.

FIG. 6 is a view showing an example of parallel display of the B mode image acquired by the Img1 and the beam profile image acquired by the Img2. FIG. 7 shows a schematic diagram of the display form in FIG. 6. The m-th direction (transmission direction) is a direction immediately under the center in both of the examples. As shown, when the beam profile image is compared with the normal B mode image, an image on one scan line can be partly recognized. It is found out from the imaged range that the position and aperture width of the focus are reflected. Echoes generated by a side lobe and a grating lobe are also shown.

Figure 8:
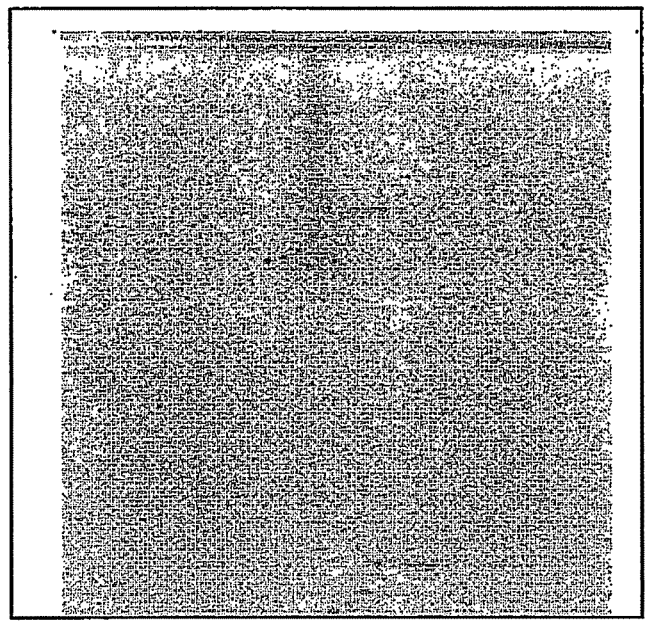
FIG. 8 is a view showing an example of a beam profile image.
Figure 9:
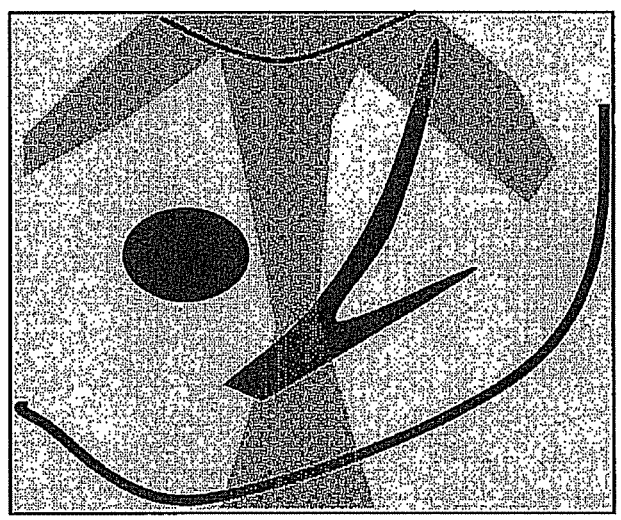
FIG. 9 is an illustration schematically showing a beam profile image.

FIG. 8 is a view showing a display form of a superposed image generated from the normal B mode image and the beam profile image. FIG. 9 shows a schematic view of the display form in FIG. 8. As shown, an image on one scan line can be partly recognized from the superposed image. It is found out from the imaged range that the position and aperture width of the focus are reflected. Echoes generated by a side lobe and a grating lobe are also shown.

(Usage Example 1)

Now, usage examples of the beam profile image or the superposed image are described.

By using the beam profile image or the superposed image acquired by the present ultrasonic diagnostic apparatus, a real focal position of the transmission beam and the shape of a sound field can be known. The control processor 28 extracts a region having a luminance equal to or more than a certain value on, for example, the beam profile image, measures the width (length in a direction perpendicular to the transmission direction) of this region, and displays a depth having the minimum width on the monitor 14 as a focal position (focal depth). As a result, the operator can visually recognize, rapidly and easily, the relation between a focal position set as a transmission condition and a real focal position within the subject.

(Usage Example 2)

By using the beam profile image or the superposed image acquired by the present ultrasonic diagnostic apparatus, an actual sound velocity of a medium can be estimated.

In general, the transmission delay of the ultrasonic diagnostic apparatus is designed to converge toward a theoretical focal position on the basis of a previously assumed sound velocity value. However, when a sound velocity within the subject is different from the assumed value, the theoretical focal position is different from a real focal position.

Thus, the present ultrasonic diagnostic apparatus estimates a precise sound velocity within the subject by the following technique that uses the beam profile image. That is, the control processor 28 changes the previously assumed sound velocity value as needed to execute the Img2 by use of a predetermined algorithm, acquires a beam profile image for each sound velocity value, and measures a real focal position corresponding to each sound velocity value in accordance with, for example, the technique shown in Usage example 1. The control processor 28 determines a real focal position that coincides with the theoretical focal position among the measured real focal positions, and estimates a sound velocity value corresponding to this focal position to be a real sound velocity value within the subject. The estimated real sound velocity value is displayed on the monitor 14 in a predetermined form. Thereafter, the use of the estimated real sound velocity value enables a more precise ultrasonic image diagnosis of the subject.

(Usage Example 3)

Various methods have been contrived to analyze a feature amount of a living body by use of an ultrasonic received signal. For example, according to a technique described in Jpn. Pat. Appln. KOKAI Publication No. 2003-61964, analysis of a statistic of an echo signal makes it possible to judge whether a dot-like pattern visible on an image is a signal reflecting an actual microstructure or a pattern (referred to as a speckle pattern) generated by a simple interference fringe.

However, the accuracy of, for example, the statistic analysis, when conducted, greatly depends on the signal to noise ratio (S/N) of a received signal. For example, the accuracy of an analytic result deteriorates when a noise component contained in the received signal is considerably great or when artifacts from other directions are mixed.

If the beam profile image or the superposed image acquired by the present ultrasonic diagnostic apparatus is used in such an analysis, the accuracy of an analytic result can be evaluated. That is, the control processor 28 extracts a main signal component in a main lobe (main beam) direction (i.e., the transmission direction) and noise signal components in other regions including a side lobe and a grating lobe, and calculates their intensity ratio to evaluate the S/N ratio of the main signal component. As a result, when, for example, the S/N ratio of the main signal component in the main beam direction is evaluated to be lower than a predetermined threshold, the control processor 28 displays, on the monitor 14, a message that says, for example, "Accuracy of analysis is affected".

Alternatively, the intensity ratio of the main signal component to the noise signal components may be displayed on the monitor 14 as required. For example, when the noise signal components account for 30% of the main signal component, it can be said that the noise signal components are predominant. By visually recognizing the intensity ratio of the main signal component to the noise signal components displayed on the monitor 14, the operator can appreciate that a satisfactory analysis can not be made in this condition, and can make an improvement by changing the radiation angle of the probe. Moreover, when an improvement is made by changing the radiation angle of the probe as mentioned above, how the transmission beam enters the subject can be visually recognized rapidly and easily by real-time display of the superposed image, so that the improvement can be recognized at a glance.

(Usage Example 4)

The beam profile image or the superposed image acquired by the present ultrasonic diagnostic apparatus can also be used for education concerning the operation of the ultrasonic diagnostic apparatus. For example, a rough shape of a transmission sound field can be visually recognized by observing the displayed beam profile image or superposed image, so that it is possible to know where a focal position or focal region is actually located and know whether the transmission sound field is larger or smaller than what has been imagined. Alternatively, it is possible to know the correspondence or difference between the theoretical focal position and the real focal position within the subject. Thus, an operator such as a doctor or an engineer can intuitively and objectively know the relation between set values of various parameters, the actual spatial resolution of ultrasonic waves within the subject, and the position and size of the focus. As a result, it is possible to assist in nurturing the sense of properly setting the various parameters of the ultrasonic diagnostic apparatus.

(Usage Example 5)

The beam profile image or the superposed image acquired by the present ultrasonic diagnostic apparatus can also be used as assistant information for an inspection to find out whether the ultrasonic diagnostic apparatus or the ultrasonic probe is functioning normally. For example, using a predetermined phantom (a model for use in an operation test of the apparatus), an ideal beam profile image for each scan line direction is acquired in advance in accordance with predetermined transmission/reception conditions. When the ideal beam profile image and a beam profile image acquired by using the same phantom and the same transmission/reception conditions are displayed in parallel or displayed in a superposed state and compared with each other, it is possible to visually judge whether the ultrasonic probe or the ultrasonic diagnostic apparatus is functioning normally.

(Advantages)

According to the present ultrasonic diagnostic apparatus described above, a transmission beam having a transmission direction and a transmission focus that are fixed is transmitted, and patterns of reception delays are changed and added, pattern by pattern, to echo signals of ultrasonic transducers obtained by using the transmission beam, such that reception beams different in receiving direction and reception focus are acquired. The echo signal for each scan line thus acquired is formed into an image to generate a beam profile image of the transmission beam in a predetermined transmission direction. If similar processing is performed for each transmission direction, a beam profile image of the transmission beam for each scan line is generated. A predetermined color or luminance is assigned to the generated beam profile image, and the beam profile image is independently displayed, or displayed in parallel with the (normal) B mode image of the same section, or displayed in such a manner as to be superposed on the B mode image. By observing the displayed beam profile image or superposed image, an operator such as a doctor or an engineer can visually recognize a rough shape of a transmission sound field, and know where the focal position or focal region is actually located and know whether the transmission sound field is larger or smaller than what has been imagined. Consequently, it is possible to intuitively and objectively know the relation between the spatial resolution and the position and size of the focus, or the limit of the spatial resolution, and avoid overestimation or underestimation of an image diagnosis.

Furthermore, by observing the superposed image in which the beam profile image is superposed on the B mode image, how the transmission beam enters the subject can be visually recognized. Thus, for example, when the transmission beam is extremely disturbed by the intercostals or peritoneum or when there is a large reflector such as a gas in the side lobe direction, it is possible to directly appreciate whether the transmission beam properly enters the subject. The entry condition of the transmission beam can be used to judge the quality (accuracy) of the extracted feature amount, for example, in evaluating the real focal position or the sound velocity value, or in analyzing the echo signal to extract a predetermined feature amount.

(Second Embodiment)

Now, an ultrasonic diagnostic apparatus according to the second embodiment is described. In the first embodiment, an echo signal before a reception delay is stored in the memory for each channel, and the echo signal is added to each of the different reception delay patterns, thereby generating reception beams different in receiving direction and reception focus. On the other hand, an ultrasonic diagnostic apparatus 1 according to the present embodiment acquires beam profile image data by alternating ultrasonic wave transmission having a transmission direction and a transmission focus that remain fixed and ultrasonic wave reception having a receiving direction and a reception focus that are being changed (i.e., having a reception delay pattern that is changed with time).

When compared, beam profile image generating/displaying processing according to the present embodiment and the beam profile image generating/displaying processing according to the first embodiment are only different in the contents of the processing in the "acquisition of beam profile image data" in step Sa2. "Acquisition of beam profile image data" according to the present embodiment is described below.

Figure 10:
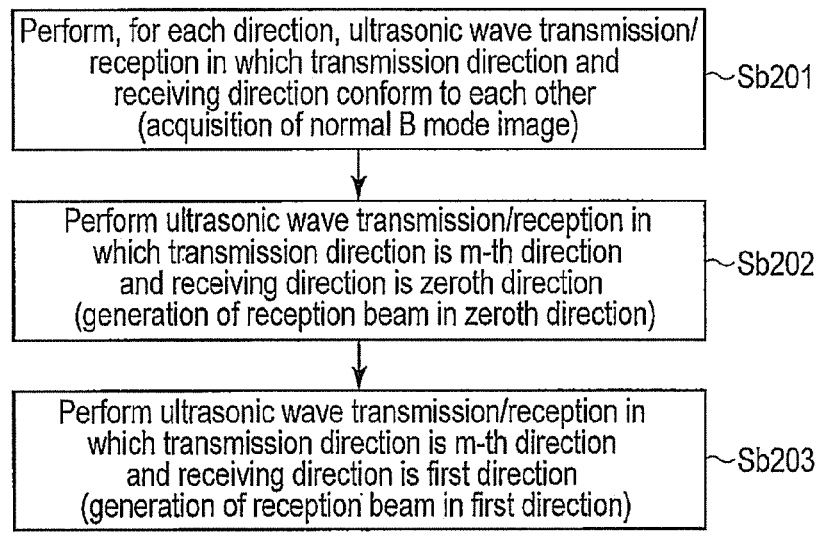
FIG. 10 is a flowchart showing the flow of beam profile image generating/displaying processing according to a second embodiment.
Figure 11:
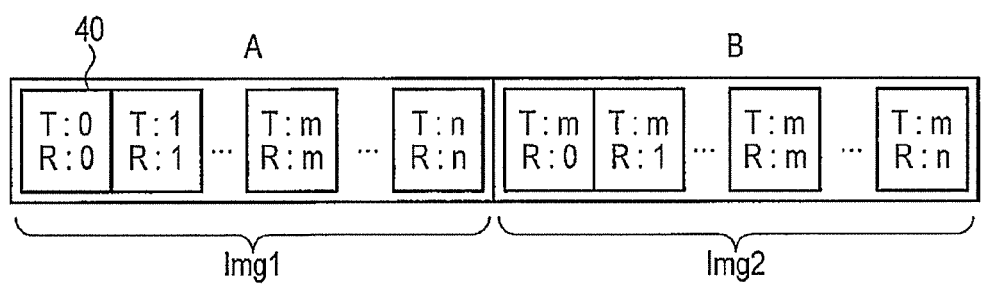
FIG. 11 is a diagram for illustrating the concept of the beam profile image acquiring processing according to the second embodiment.

FIG. 10 is a flowchart showing the flow of the beam profile image data acquiring processing according to the second embodiment. FIG. 11 is a diagram for illustrating the concept of the beam profile image data acquiring processing.

First, a control processor 28 performs ultrasonic wave transmission/reception in which the transmission direction and the receiving direction conform to each other (i.e., normal ultrasonic wave transmission/reception) for each of the n+1 scan lines corresponding to the scan line numbers zero to n (step Sb201). This transmission/reception is indicated as ultrasonic imaging (Img1) corresponding to a block A in FIG. 11. Normal B mode image data is acquired by the Img1.

Furthermore, ultrasonic wave transmission/reception in which the m-th direction is the transmission direction and, for example, the zeroth direction is the receiving direction is performed (step Sb202). That is, as shown in FIG. 11, ultrasonic wave transmission/reception in which a transmission delay in the m-th direction and a reception delay in the zeroth direction are set is performed. The reception delay in the zeroth direction is added to an echo signal acquired by the transmission/reception in the reception delay unit, so that an echo signal (reception beam) in which the zeroth direction is the scan line is generated.

Furthermore, ultrasonic wave transmission/reception in which the m-th direction is the transmission direction and, for example, the first direction is the receiving direction is performed (step Sb203). That is, ultrasonic wave transmission/reception in which a transmission delay in the m-th direction and a reception delay in the first direction are set is performed. The reception delay in the first direction is added to an echo signal acquired by the transmission/reception in the reception delay unit, so that an echo signal (reception beam) in which the first direction is the scan line is generated. Similarly, the control processor 28 alternately performs ultrasonic wave transmission/reception in which the m-th direction is the transmission direction and the receiving direction is the second direction (or the third direction, the fourth direction . . . , the n-th direction), and acquires an echo signal regarding each receiving direction (each scan line direction) for a transmission beam in which the transmission direction is fixed to the m-th direction. The generation of the echo signal for each receiving direction is indicated as ultrasonic imaging (Img2) corresponding to a block B in FIG. 11. The Img2 acquires image (beam profile image) data correlated with a sound field beam profile for the transmission in the m-th direction.

The second embodiment is similar to the first embodiment in that beam profile image data can be acquired for transmission beams of the other directions if similar processing is performed by setting Img3, Img4 . . . .

The configuration described above can be used in a similar manner as the first embodiment and provide similar advantages. Moreover, in the present embodiment, transmission is sequentially performed, so that the time required for the Img2 is substantially the same as the time required for the Img1 (for acquiring the normal B mode image). However, the method according to the present embodiment does not need a special memory after a preamplifier, and therefore advantageously allows for a simpler circuit configuration.

The present embodiment is not completely limited to the embodiments described above, and the components can be modified at the stage of carrying out the embodiment without departing from the spirit thereof. The following modifications are shown as specific modifications by way of example.

(1) The functions according to the present embodiment can be provided by installing programs for executing this processing into a computer of, for example, a work station and expanding the programs on a memory. In this case, the programs that enable the computer to perform such a method can be stored in a recording medium such as a magnetic disk (e.g., a floppy (registered trademark) disk or a hard disk), an optical disk (e.g., a CD-ROM or a DVD), or a semiconductor memory, and distributed.

(2) In the examples described in the above embodiments, a beam profile image as a two-dimensional image is generated and displayed when a two-dimensional region is ultrasonically scanned. However, the technical concept of the present embodiment is not limited to the two-dimensional case, and is also applicable to, for example, a three-dimensional ultrasonic imaging method which three-dimensionally scans a subject to acquire volume data and generates a three-dimensional diagnostic image from the data. In this case, a three-dimensional beam profile image can be acquired by, for example, beam transmission in which the transmission direction is fixed to the m-th direction and beam reception that uses a reception delay pattern for each of the receiving directions having a three-dimensional azimuth (that is not limited to the same plane). When the three-dimensional ultrasonic scan is performed in this manner, an oscillating probe obtained by mechanically oscillating one-dimensionally arranged transducers or a matrix array probe in which ultrasonic transducers are two-dimensionally arranged is used as the ultrasonic probe 12.

(3) The beam profile image can also be generated and displayed by an ultrasonic image processing apparatus that is obtained by, for example, a work station. That is, an echo signal obtained by a transmission beam in which the transmission direction is the m-th direction is stored for each channel before reception and addition. This echo signal is read in an after-the-fact manner, and reception delay patterns corresponding to the receiving directions are used and added. As a result, an echo signal (reception beam) for each scan line direction can be generated.

(4) In the examples shown in the above embodiments, echo signals are acquired by using all the ultrasonic transducers of the ultrasonic probe, and each echo signal is used to generate a beam profile image. However, the present embodiment is not limited to this example. For example, as in a sparse array probe, echo signals are acquired by using some of all the ultrasonic transducers (i.e., by thinning out the ultrasonic transducers), and the acquired echo signals can be used to generate a beam profile image. Otherwise, echo signals are acquired by using all the ultrasonic transducers or some of all the ultrasonic transducers of the ultrasonic probe, and some of the acquired echo signals can be used (i.e., the echo signals can be thinned out) to generate a beam profile image.

Furthermore, various inventions can be made by a proper combination of the components disclosed in the embodiments described above. For example, some of all the components shown in the embodiments may be eliminated. Moreover, the components in different embodiments may be properly combined together.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
    ultrasonic transducers, each of the ultrasonic transducers generating an ultrasonic wave in response to a supplied drive signal, and generating an echo signal in response to a received ultrasonic wave;
    transmission circuitry which supplies the drive signal to at least some of the ultrasonic transducers to transmit a transmission beam associated with a predetermined transmission focal position from the ultrasonic probe;
    receiving circuitry which performs a delay addition processing for echo signals generated by at least some of the ultrasonic transducers and acquires reception beams associated with predetermined reception focal positions by the delay addition processing;
    input circuitry which receives designations of a beam profiling mode and at least a transmission focal position;
    processing circuitry which generates a B mode image by performing a B mode process including logarithmic amplification and envelope detection to reception beams based on transmission beams associated with a plurality of transmission focal positions, and generates a beam profile image by performing the B mode process to reception beams based on transmission beams associated with a fixed transmission focal position, the beam profile image being an image regarding sound field for the transmission beam to represent a rough shape of a transmission sound field;
    extracts a region having a luminance equal to or more than a certain value on the beam profile image,
    measures a minimum width of the region, the minimum width indicating a length in a direction perpendicular to a transmission direction, and
    measures a depth having the minimum width as information on the fixed transmission focal position; and
    a display which displays the beam profile image, the measured information on the fixed transmission focal position, the predetermined transmission focal position and the B mode image as a display of the beam profiling mode.

2. The ultrasonic diagnostic apparatus according to claim 1, wherein the receiving circuitry comprises a recording circuitry to record, before the addition, each of the echo signals for each of the ultrasonic transducers obtained by use of the transmission beam including the transmission direction and the transmission focus that are fixed, and further comprising control circuitry which controls the transmission circuitry so as to transmit the transmission beam associated with the designated transmission focal position after the designations and controls the receiving circuitry by changing the patterns of the reception delays and adding each of the patterns to each of the echo signals for each of the ultrasonic transducers recorded before the addition in order to acquire the reception beams different in the receiving direction and the reception focus.

3. The ultrasonic diagnostic apparatus according to claim 2, wherein the control circuitry controls the transmission circuitry and the receiving circuitry to alternately repeat the transmission of the transmission beam including the transmission direction and the transmission focus that are fixed and the acquisition of the reception beam in which the pattern of the reception delay is changed.

4. The ultrasonic diagnostic apparatus according to claim 1, wherein the processing circuitry generates a superposed image by use of the beam profile image and an ultrasonic image of a subject, and
    the display displays the superposed image.

5. The ultrasonic diagnostic apparatus according to claim 1, wherein the processing circuitry acquires the beam profile image for each sound velocity value, and measures a real focal position corresponding to the each sound velocity value,
    the apparatus further comprises an estimation circuitry which estimates a sound velocity value within a subject on the basis of the position of the set transmission focus and the position of a transmission focus estimated by use of the beam profile image,
    wherein the display displays the estimated medium sound velocity of the subject.

6. The ultrasonic diagnostic apparatus according to claim 1, further comprising a control processor which uses the beam profile image to evaluate an S/N ratio regarding a main signal component in a main lobe direction of the transmission beam,
    wherein the display displays results of the evaluation by the control processor.

7. The ultrasonic diagnostic apparatus according to claim 2, wherein the control circuitry controls the receiving circuitry by changing the patterns of the reception delays and adding each of the patterns in order to acquire reception beams two-dimensionally different in receiving direction and reception focus.

8. The ultrasonic diagnostic apparatus according to claim 2, wherein the control circuitry controls the receiving circuitry by changing the patterns of the reception delays and adding each of the patterns in order to acquire reception beams three-dimensionally different in receiving direction and reception focus.

9. The ultrasonic diagnostic apparatus according to claim 1, wherein the display displays the beam profile image in parallel with an ultrasonic image.

* * * * *